United States Patent
Mao et al.

(10) Patent No.: US 11,634,507 B2
(45) Date of Patent: Apr. 25, 2023

(54) DENDRITIC GOLD NANOPARTICLES AND METHODS OF SYNTHESIS

(71) Applicant: The Board of Regents of the University of Oklahoma, Norman, OK (US)

(72) Inventors: Chuanbin Mao, Norman, OK (US); Lin Wang, Norman, OK (US); Penghe Qiu, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 505 days.

(21) Appl. No.: 16/838,798

(22) Filed: Apr. 2, 2020

(65) Prior Publication Data

US 2021/0189012 A1    Jun. 24, 2021

Related U.S. Application Data

(60) Provisional application No. 62/831,613, filed on Apr. 9, 2019.

(51) Int. Cl.
| | | |
|---|---|---|
| *C07K 2/00* | (2006.01) | |
| *C07K 17/14* | (2006.01) | |
| *A61K 39/00* | (2006.01) | |
| *A61K 39/385* | (2006.01) | |
| *A61K 39/39* | (2006.01) | |

(52) U.S. Cl.
CPC .......... *C07K 17/14* (2013.01); *A61K 39/0011* (2013.01); *A61K 39/385* (2013.01); *A61K 39/39* (2013.01); *A61K 2039/55561* (2013.01); *A61K 2039/60* (2013.01); *A61K 2039/627* (2013.01); *A61K 2039/645* (2013.01)

(58) Field of Classification Search
CPC .................................................... C07K 17/14
See application file for complete search history.

(56) References Cited

PUBLICATIONS

Song, Chunyuan et al.; "A gold nanoflower-based traceable drug delivery system for intracellular SERS imaging-guided targeted chemo-phototherapy"; Journal of Materials Chemistry B; 6; 2018; pp. 3030-3039.

Ong, Zhan Yuin et al.; "Multibranched Gold Nanoparticles with Intrinsic LAT-1 Targeting Capabilities for Selective Photothermal Therapy of Breast Cancer"; ACS Applied Materials & Interfaces; 9; 2017; pp. 39259-39270.

Qiu, Penghe et al.; "Tuning photothermal properties of gold nanodendrites for in vivo cancer therapy within a wide near infrared range by simply controlling their degree of branching"; Biomaterials; 104; 2016; pp. 138-144.

Jia, Wenfeng et al.; "Synthesis of Highly Branched Gold Nanodendrites with a Narrow Size Distribution and Tunable NIR and SERS Using a Multiamine Surfactant"; ACS Applied Materials & Interfaces; 5; 2013; pp. 6886-6892.

*Primary Examiner* — Albert M Navarro
(74) *Attorney, Agent, or Firm* — Winstead PC

(57) ABSTRACT

A method of producing dendritic gold nanoparticles by combining a gold precursor solution, a reducing agent, and a bifunctional peptide having an amine-rich amino acid sequence into a buffered aqueous solution in a single container, and agitating the mixture causing the formation of the dendritic gold nanoparticles having a surface with a positive charge and a second end portion of the bifunctional peptide exposed on the surface of the dendritic gold nanoparticles. The dendritic gold nanoparticles may be used to deliver therapeutic, diagnostic, and/or immunogenic amino acid sequences as portions of the bifunctional peptide.

7 Claims, 5 Drawing Sheets

Specification includes a Sequence Listing.

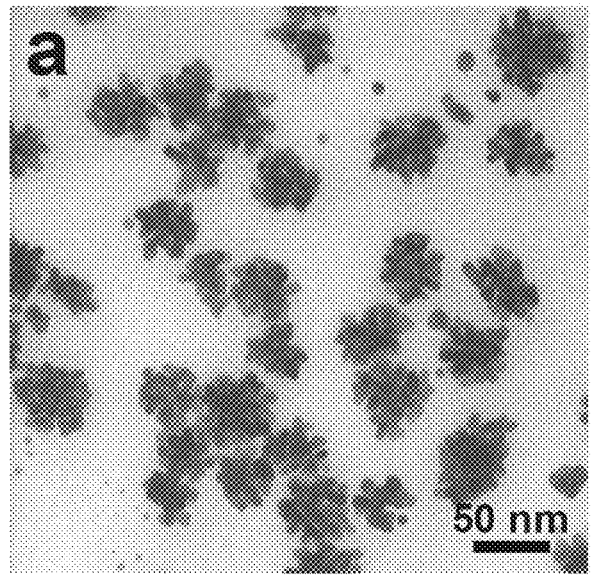
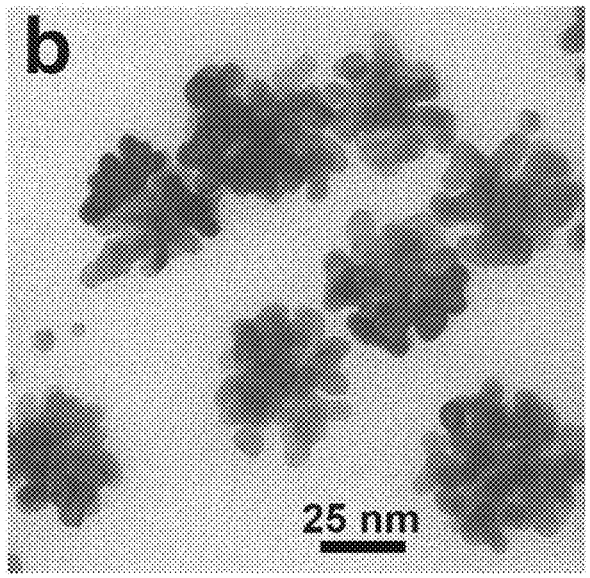
FIG. 1a FIG. 1b
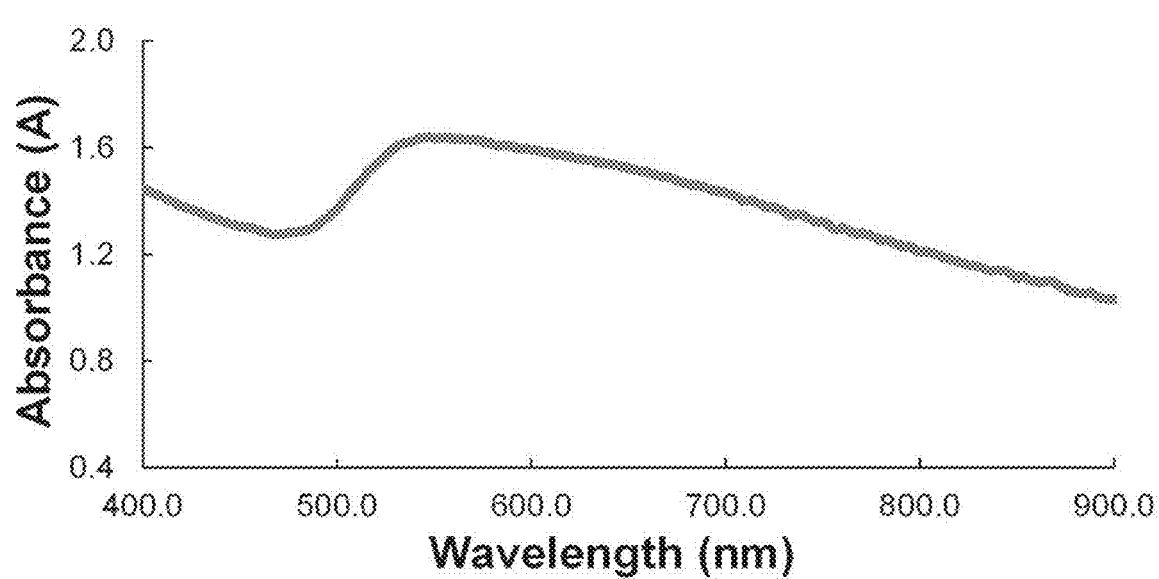
FIG. 2 structural segment structural segment+G23 functional segment no peptide

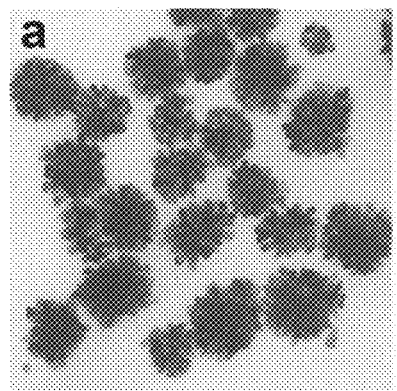 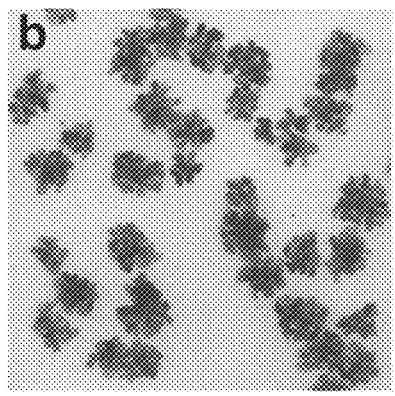 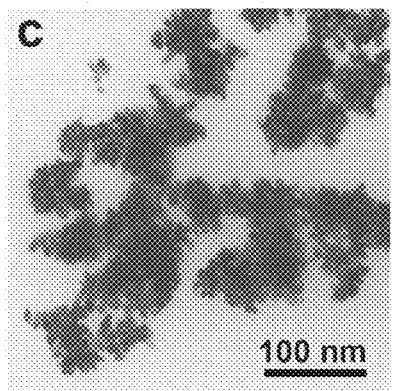
FIG. 4a     FIG. 4b     FIG. 4c
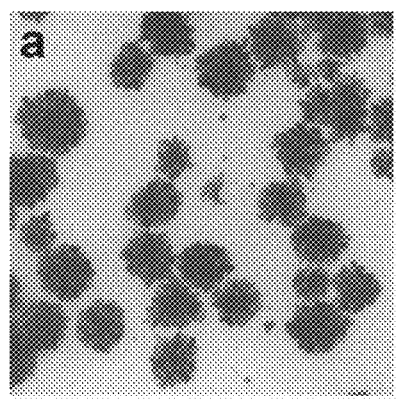 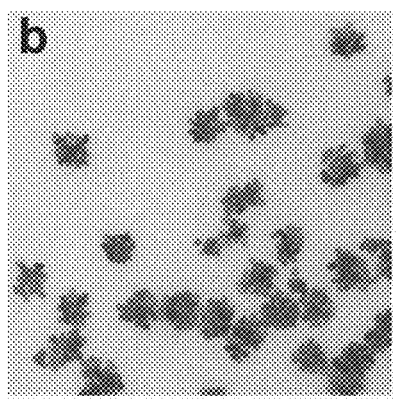 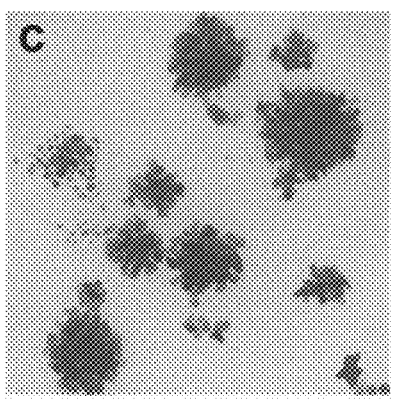
FIG. 5a (MBP)     FIG. 5b (Ctrl)     FIG. 5c (Tau)
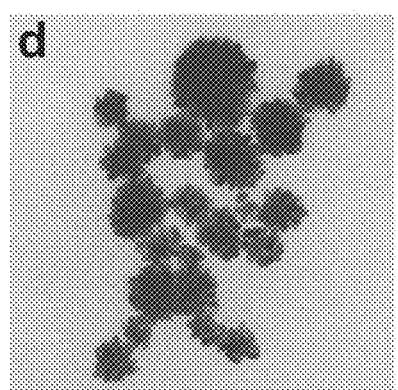 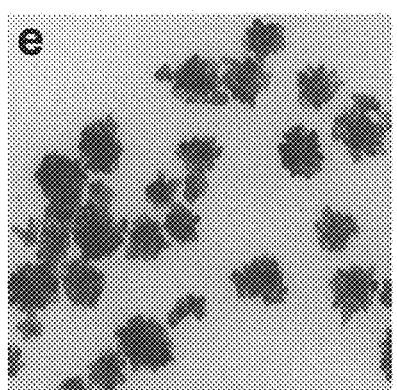 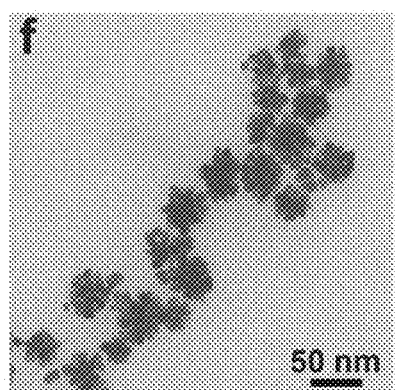
FIG. 5d (Gp100)     FIG. 5e (CTIP)     FIG. 5f (Self)

SEQUENCE LISTING

```
<160> NUMBER OF SEQ ID NOS: 83

<210> SEQ ID NO 1
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 1

Arg Arg Arg Arg Arg Arg Arg Arg
1               5

<210> SEQ ID NO 2
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 2

Arg Arg Arg Arg Arg Arg Arg Lys
1               5

<210> SEQ ID NO 3
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 3

Lys Arg Arg Arg Arg Arg Arg Arg
1               5

<210> SEQ ID NO 4
<211> LENGTH: 8
<212> TYPE: PRT
<213> ORGANISM: Artificial Sequence
<220> FEATURE:
<223> OTHER INFORMATION: 8-mer Structural (amine-rich) Peptide
```

<400> SEQUENCE: 4

Lys Arg Arg Arg Arg Arg Arg Lys
1               5

<210> SEQ ID NO 5
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 5

Arg Lys Arg Arg Arg Arg Lys Arg
1               5

<210> SEQ ID NO 6
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 6

Arg Arg Lys Arg Arg Lys Arg Arg
1               5

<210> SEQ ID NO 7
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 7

Arg Arg Arg Lys Lys Arg Arg Arg
1               5

<210> SEQ ID NO 8
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 8

Arg Lys Lys Arg Arg Lys Lys Arg
1               5

<210> SEQ ID NO 9
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 9

Lys Arg Lys Arg Lys Arg Lys Arg
1               5

<210> SEQ ID NO 10
<211> LENGTH: 8
<212> TYPE: PRT
<213> ORGANISM: Artificial Sequence
<220> FEATURE:
<223> OTHER INFORMATION: 8-mer Structural (amine-rich) Peptide

```
<400> SEQUENCE: 10

Arg Lys Arg Lys Arg Lys Arg Lys
1               5

<210> SEQ ID NO 11
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 11

Arg Arg Arg Lys Lys Arg Arg Lys
1               5

<210> SEQ ID NO 12
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 12

Lys Arg Arg Lys Lys Arg Arg Arg
1               5

<210> SEQ ID NO 13
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 13

Arg Arg Arg Lys Lys Arg Arg Lys
1               5

<210> SEQ ID NO 14
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 14

Lys Arg Arg Lys Lys Arg Arg Arg
1               5

<210> SEQ ID NO 15
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 15

Arg Arg Arg Arg Lys Lys Lys Lys
1               5

<210> SEQ ID NO 16
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 16
```

```
Arg Lys Lys Lys Lys Lys Lys Arg
1               5
```

<210> SEQ ID NO 17
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 17

```
Arg Arg Arg Arg Arg Arg Arg His
1               5
```

<210> SEQ ID NO 18
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 18

```
His Arg Arg Arg Arg Arg Arg Arg
1               5
```

<210> SEQ ID NO 19
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 19

```
His Arg Arg Arg Arg Arg Arg His
1               5
```

<210> SEQ ID NO 20
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 20

```
Arg His Arg Arg Arg Arg His Arg
1               5
```

<210> SEQ ID NO 21
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 21

```
Arg Arg His Arg Arg His Arg Arg
1               5
```

<210> SEQ ID NO 22
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 22

Arg Arg Arg His His Arg Arg Arg
1               5

<210> SEQ ID NO 23
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 23

Arg His His Arg Arg His His Arg
1               5

<210> SEQ ID NO 24
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 24

His Arg His Arg His Arg His Arg
1               5

<210> SEQ ID NO 25
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 25

Arg His Arg His Arg His Arg His
1               5

<210> SEQ ID NO 26
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 26

Arg Arg Arg His His Arg Arg His
1               5

<210> SEQ ID NO 27
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 27

His Arg Arg His His Arg Arg Arg
1               5

<210> SEQ ID NO 28
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 28

Arg Arg Arg His His Arg Arg His

```
<210> SEQ ID NO 29
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 29

His Arg Arg His His Arg Arg Arg
1               5

<210> SEQ ID NO 30
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 30

Arg Arg Arg Arg His His His His
1               5

<210> SEQ ID NO 31
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 31

Arg His His His His His His Arg
1               5

<210> SEQ ID NO 32
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 32

His His His His His His His His
1               5

<210> SEQ ID NO 33
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 33

Lys Lys Lys Lys Lys Lys Lys Lys
1               5

<210> SEQ ID NO 34
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 34

Lys Lys Lys Lys Lys Lys Lys His
1               5
```

```
<210> SEQ ID NO 35
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 35

His Lys Lys Lys Lys Lys Lys Lys
1               5

<210> SEQ ID NO 36
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 36

His Lys Lys Lys Lys Lys Lys His
1               5

<210> SEQ ID NO 37
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 37

Lys His Lys Lys Lys Lys His Lys
1               5

<210> SEQ ID NO 38
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 38

Lys Lys His Lys Lys His Lys Lys
1               5

<210> SEQ ID NO 39
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 39

Lys Lys Lys His His Lys Lys Lys
1               5

<210> SEQ ID NO 40
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 40

Lys His His Lys Lys His His Lys
1               5
```

```
<210> SEQ ID NO 41
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 41

His Lys His Lys His Lys His Lys
1               5

<210> SEQ ID NO 42
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 42

Lys His Lys His Lys His Lys His
1               5

<210> SEQ ID NO 43
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 43

Lys Lys Lys His His Lys Lys His
1               5

<210> SEQ ID NO 44
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 44

His Lys Lys His His Lys Lys Lys
1               5

<210> SEQ ID NO 45
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 45

Lys Lys Lys His His Lys Lys His
1               5

<210> SEQ ID NO 46
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 46

His Lys Lys His His Lys Lys Lys
1               5
```

-continued

```
<210> SEQ ID NO 47
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 47

Lys Lys Lys Lys His His His His
1               5

<210> SEQ ID NO 48
<211> LENGTH: 8
<212> TYPE: PRT
<213> ORGANISM: Artificial Sequence
<220> FEATURE:
<223> OTHER INFORMATION: 8-mer Structural (amine-rich) Peptide

<400> SEQUENCE: 48

Lys His His His His His His Lys
1               5

<210> SEQ ID NO 49
<211> LENGTH: 4
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(4)
<223> OTHER INFORMATION: Each of Xaa is Independently Selected from Arg
      (R), Lys (K), and His (H)

<400> SEQUENCE: 49

Xaa Xaa Xaa Xaa
1

<210> SEQ ID NO 50
<211> LENGTH: 5
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(5)
<223> OTHER INFORMATION: Each of Xaa is Independently Selected from Arg
      (R), Lys (K), and His (H)

<400> SEQUENCE: 50

Xaa Xaa Xaa Xaa Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(6)
<223> OTHER INFORMATION: Each of Xaa is Independently Selected from Arg
      (R), Lys (K), and His (H)

<400> SEQUENCE: 51

Xaa Xaa Xaa Xaa Xaa Xaa
1               5
```

```
<210> SEQ ID NO 52
<211> LENGTH: 7
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(7)
<223> OTHER INFORMATION: Each of Xaa is Independently Selected from Arg
      (R), Lys (K), and His (H)

<400> SEQUENCE: 52

Xaa Xaa Xaa Xaa Xaa Xaa Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(8)
<223> OTHER INFORMATION: Each of Xaa is Independently Selected from Arg
      (R), Lys (K), and His (H)

<400> SEQUENCE: 53

Xaa Xaa Xaa Xaa Xaa Xaa Xaa Xaa
1               5

<210> SEQ ID NO 54
<211> LENGTH: 9
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(9)
<223> OTHER INFORMATION: Each of Xaa is Independently Selected from Arg
      (R), Lys (K), and His (H)

<400> SEQUENCE: 54

Xaa Xaa Xaa Xaa Xaa Xaa Xaa Xaa Xaa
1               5

<210> SEQ ID NO 55
<211> LENGTH: 10
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(10)
<223> OTHER INFORMATION: Each of Xaa is Independently Selected from Arg
      (R), Lys (K), and His (H)

<400> SEQUENCE: 55

Xaa Xaa Xaa Xaa Xaa Xaa Xaa Xaa Xaa Xaa
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Structural Peptide
```

```
<220> FEATURE:
<221> NAME/KEY: MISC_FEATURE
<222> LOCATION: (1)..(11)
<223> OTHER INFORMATION: Each of Xaa is Independently Selected from Arg
      (R), Lys (K), and His (H)

<400> SEQUENCE: 56

Xaa Xaa Xaa Xaa Xaa Xaa Xaa Xaa Xaa Xaa Xaa
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(12)
<223> OTHER INFORMATION: Each of Xaa is Independently Selected from Arg
      (R), Lys (K), and His (H)

<400> SEQUENCE: 57

Xaa Xaa Xaa Xaa Xaa Xaa Xaa Xaa Xaa Xaa Xaa Xaa
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(13)
<223> OTHER INFORMATION: Each of Xaa is Independently Selected from Arg
      (R), Lys (K), and His (H)

<400> SEQUENCE: 58

Xaa Xaa Xaa Xaa Xaa Xaa Xaa Xaa Xaa Xaa Xaa Xaa Xaa
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(14)
<223> OTHER INFORMATION: Each of Xaa is Independently Selected from Arg
      (R), Lys (K), and His (H)

<400> SEQUENCE: 59

Xaa Xaa Xaa Xaa Xaa Xaa Xaa Xaa Xaa Xaa Xaa Xaa Xaa Xaa
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(15)
<223> OTHER INFORMATION: Each of Xaa is Independently Selected from Arg
      (R), Lys (K), and His (H)

<400> SEQUENCE: 60
```

-continued

Xaa Xaa Xaa Xaa Xaa Xaa Xaa Xaa Xaa Xaa Xaa Xaa Xaa Xaa Xaa
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Structural Peptide
<220> FEATURE:
<221> NAME/KEY: MISC_FEATURE
<222> LOCATION: (1)..(16)
<223> OTHER INFORMATION: Each of Xaa is Independently Selected from Arg
      (R), Lys (K), and His (H)

<400> SEQUENCE: 61

Xaa Xaa Xaa Xaa Xaa Xaa Xaa Xaa Xaa Xaa Xaa Xaa Xaa Xaa Xaa Xaa
1               5                   10                  15

<210> SEQ ID NO 62
<211> LENGTH: 20
<212> TYPE: PRT
<213> ORGANISM: Artificial Sequence
<220> FEATURE:
<223> OTHER INFORMATION: NFL

<400> SEQUENCE: 62

Tyr Ser Ser Ser Ala Pro Val Ser Ser Ser Val Arg Arg Ser Tyr Ser
1               5                   10                  15

Ser Ser Gly Ser
            20

<210> SEQ ID NO 63
<211> LENGTH: 20
<212> TYPE: PRT
<213> ORGANISM: Artificial Sequence
<220> FEATURE:
<223> OTHER INFORMATION: G23

<400> SEQUENCE: 63

Gly Gly Gly Gly Gly Gly Gly Gly Gly Gly Gly Gly Gly Gly Gly Gly
1               5                   10                  15

Gly Gly Gly Gly
            20

<210> SEQ ID NO 64
<211> LENGTH: 15
<212> TYPE: PRT
<213> ORGANISM: Artificial Sequence
<220> FEATURE:
<223> OTHER INFORMATION: MBP

<400> SEQUENCE: 64

Ala Arg Glu Tyr Gly Thr Arg Phe Ser Leu Ile Gly Gly Tyr Arg
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Ctrl

<400> SEQUENCE: 65

Arg Gly Ile Glu Phe Tyr Gly Arg Ser Thr Leu Ala Ala Gly Arg
1               5                   10                  15

```
<210> SEQ ID NO 66
<211> LENGTH: 9
<212> TYPE: PRT
<213> ORGANISM: Artificial Sequence
<220> FEATURE:
<223> OTHER INFORMATION: Gp100

<400> SEQUENCE: 66

Ile Met Asp Gln Val Pro Phe Ser Val
1               5

<210> SEQ ID NO 67
<211> LENGTH: 15
<212> TYPE: PRT
<213> ORGANISM: Artificial Sequence
<220> FEATURE:
<223> OTHER INFORMATION: Tau

<400> SEQUENCE: 67

Val Gln Ile Ile Asn Lys Lys Leu Asp Leu Ser Asn Val Gln Ser
1               5                   10                  15

<210> SEQ ID NO 68
<211> LENGTH: 8
<212> TYPE: PRT
<213> ORGANISM: Artificial Sequence
<220> FEATURE:
<223> OTHER INFORMATION: CTIP

<400> SEQUENCE: 68

Asp Gly Ser Ile Pro Trp Ser Thr
1               5

<210> SEQ ID NO 69
<211> LENGTH: 20
<212> TYPE: PRT
<213> ORGANISM: Artificial Sequence
<220> FEATURE:
<223> OTHER INFORMATION: Self

<400> SEQUENCE: 69

Asn Tyr Thr Cys Glu Val Thr Glu Leu Thr Arg Glu Gly Glu Thr Ile
1               5                   10                  15

Ile Glu Leu Lys
            20

<210> SEQ ID NO 70
<211> LENGTH: 25
<212> TYPE: PRT
<213> ORGANISM: Artificial Sequence
<220> FEATURE:
<223> OTHER INFORMATION: Dermicidin

<400> SEQUENCE: 70

Ser Ser Leu Leu Glu Lys Gly Leu Asp Gly Ala Lys Lys Ala Val Gly
1               5                   10                  15

Gly Leu Gly Lys Leu Gly Lys Asp Ala
            20                  25

<210> SEQ ID NO 71
<211> LENGTH: 17
<212> TYPE: PRT
<213> ORGANISM: Artificial Sequence
<220> FEATURE:
<223> OTHER INFORMATION: OVA
```

-continued

<400> SEQUENCE: 71

Ile Ser Gln Ala Val His Ala Ala His Ala Glu Ile Asn Glu Ala Gly
1               5                   10                  15

Arg

<210> SEQ ID NO 72
<211> LENGTH: 4
<212> TYPE: PRT
<213> ORGANISM: Artificial Sequence
<220> FEATURE:
<223> OTHER INFORMATION: Linker

<400> SEQUENCE: 72

Gly Gly Gly Gly
1

<210> SEQ ID NO 73
<211> LENGTH: 31
<212> TYPE: PRT
<213> ORGANISM: Artificial Sequence
<220> FEATURE:
<223> OTHER INFORMATION: R8+NFL

<400> SEQUENCE: 73

Arg Arg Arg Arg Arg Arg Arg Arg Gly Gly Tyr Ser Ser Ser Ala
1               5                   10                  15

Pro Val Ser Ser Ser Val Arg Arg Ser Tyr Ser Ser Ser Gly Ser
            20                  25                  30

<210> SEQ ID NO 74
<211> LENGTH: 26
<212> TYPE: PRT
<213> ORGANISM: Artificial Sequence
<220> FEATURE:
<223> OTHER INFORMATION: MBP+R8

<400> SEQUENCE: 74

Ala Arg Glu Tyr Gly Thr Arg Phe Ser Leu Ile Gly Gly Tyr Arg Gly
1               5                   10                  15

Gly Gly Arg Arg Arg Arg Arg Arg Arg Arg
            20                  25

<210> SEQ ID NO 75
<211> LENGTH: 26
<212> TYPE: PRT
<213> ORGANISM: Artificial Sequence
<220> FEATURE:
<223> OTHER INFORMATION: Ctrl+R8

<400> SEQUENCE: 75

Arg Gly Ile Glu Phe Tyr Gly Arg Ser Thr Leu Ala Ala Gly Arg Gly
1               5                   10                  15

Gly Gly Arg Arg Arg Arg Arg Arg Arg Arg
            20                  25

<210> SEQ ID NO 76
<211> LENGTH: 20
<212> TYPE: PRT
<213> ORGANISM: Artificial Sequence
<220> FEATURE:
<223> OTHER INFORMATION: R8+Gp100

<400> SEQUENCE: 76

Arg Arg Arg Arg Arg Arg Arg Arg Gly Gly Gly Ile Met Asp Gln Val
1               5                   10                  15

Pro Phe Ser Val
            20

<210> SEQ ID NO 77
<211> LENGTH: 26
<212> TYPE: PRT
<213> ORGANISM: Artificial Sequence
<220> FEATURE:
<223> OTHER INFORMATION: R8+Tau

<400> SEQUENCE: 77

Arg Arg Arg Arg Arg Arg Arg Arg Gly Gly Gly Val Gln Ile Ile Asn
1               5                   10                  15

Lys Lys Leu Asp Leu Ser Asn Val Gln Ser
            20                  25

<210> SEQ ID NO 78
<211> LENGTH: 32
<212> TYPE: PRT
<213> ORGANISM: Artificial Sequence
<220> FEATURE:
<223> OTHER INFORMATION: R8+Self

<400> SEQUENCE: 78

Arg Arg Arg Arg Arg Arg Arg Arg Gly Gly Gly Gly Asn Tyr Thr Cys
1               5                   10                  15

Glu Val Thr Glu Leu Thr Arg Glu Gly Glu Thr Ile Ile Glu Leu Lys
            20                  25                  30

<210> SEQ ID NO 79
<211> LENGTH: 36
<212> TYPE: PRT
<213> ORGANISM: Artificial Sequence
<220> FEATURE:
<223> OTHER INFORMATION: R8+Derm

<400> SEQUENCE: 79

Arg Arg Arg Arg Arg Arg Arg Arg Gly Gly Gly Ser Ser Leu Leu Glu
1               5                   10                  15

Lys Gly Leu Asp Gly Ala Lys Lys Ala Val Gly Gly Leu Gly Lys Leu
            20                  25                  30

Gly Lys Asp Ala
            35

<210> SEQ ID NO 80
<211> LENGTH: 28
<212> TYPE: PRT
<213> ORGANISM: Artificial Sequence
<220> FEATURE:
<223> OTHER INFORMATION: R8+OVA

<400> SEQUENCE: 80

Arg Arg Arg Arg Arg Arg Arg Arg Gly Gly Gly Ile Ser Gln Ala Val
1               5                   10                  15

His Ala Ala His Ala Glu Ile Asn Glu Ala Gly Arg
            20                  25

<210> SEQ ID NO 81
<211> LENGTH: 16
<212> TYPE: PRT
<213> ORGANISM: Artificial Sequence
<220> FEATURE:

-continued

```
<223> OTHER INFORMATION: CTIPs+R8

<400> SEQUENCE: 81

Asp Gly Ser Ile Pro Trp Ser Thr Arg Arg Arg Arg Arg Arg Arg
1               5                   10                  15

<210> SEQ ID NO 82
<211> LENGTH: 31
<212> TYPE: PRT
<213> ORGANISM: Artificial Sequence
<220> FEATURE:
<223> OTHER INFORMATION: G23

<400> SEQUENCE: 82

Arg Arg Arg Arg Arg Arg Arg Arg Gly Gly Gly Gly Gly Gly Gly
1               5                   10                  15

Gly Gly Gly Gly Gly Gly Gly Gly Gly Gly Gly Gly Gly Gly Gly
            20                  25                  30

<210> SEQ ID NO 83
<211> LENGTH: 9
<212> TYPE: PRT
<213> ORGANISM: Artificial Sequence
<220> FEATURE:
<223> OTHER INFORMATION: R8-Trp2

<400> SEQUENCE: 83

Ser Tyr Tyr Asp Phe Phe Val Trp Leu
1               5
```

DENDRITIC GOLD NANOPARTICLES AND METHODS OF SYNTHESIS

CROSS-REFERENCE TO RELATED APPLICATIONS

This application claims the benefit under 35 U.S.C. § 119(e) of U.S. Provisional Patent Application No. 62/831,613 filed Apr. 9, 2019, which is incorporated herein by reference in its entirety as if fully set forth herein.

STATEMENT REGARDING FEDERALLY SPONSORED RESEARCH

This invention was made with government support under Contract Number EB021339 awarded by the National Institutes of Health and Contract Number DE-SC0016567 awarded by the Department of Energy. The government has certain rights in the invention.

TECHNICAL FIELD

The present disclosure relates generally to nanoparticles and more particularly, but not by way of limitation, to dendritic gold nanoparticles and methods of synthesis and use.

BACKGROUND

Due to the complexity of the mechanism of many diseases such as cancer, the therapy strategy simply using only one type of drug or single treatment method is not sufficient. To deal with this situation, combination therapies which synergistically employ two or more types of treatments, such as surgery treatment, chemotherapy, radiotherapy, targeted therapy photothermal treatment and immunotherapy, against multiple targets or functional systems, have shown significant potential in both research and clinical applications. A powerful platform capable of integrating multiple functional components would be beneficial in the treatment of many diseases and conditions. An ideal platform would possess the following characteristics: (i) easy to fabricate, (ii) high stability, (iii) inertness to the physiological environment, (iv) integratable with multiple functions, and (v) customizable according to specific situations. Gold nanoparticles have been viewed as candidates for such a platform due to their biocompatibility and tunable optical properties. Gold dendritic nanoparticles in particular have large surface areas and wide optical bands. However, previously, this type of nanoparticle was mostly obtained from organic phase synthesis. Moreover, to be equipped with bioactivity for therapeutic applications, tedious multiple-step phase transfer and surface ligand-exchange procedures have been required. This has often resulted in the diminishment of the density of the active particles on the surfaces of the nanoparticles and reductions in their stability. Improvements in methods of gold nanodentrite synthesis and functionalization and their uses have thus been sought. It is to this end that the present disclosure is directed.

SUMMARY OF THE INVENTION

In an embodiment, the present disclosure relates to a method of producing dendritic gold nanoparticles. In some embodiments, the method includes providing a gold precursor solution, a reducing agent, and a bifunctional peptide. In some embodiments, the bifunctional peptide includes a first end portion including an amine-rich amino acid sequence, and a second end portion. In some embodiments, the method further includes combining, in a single container, the gold precursor solution, reducing agent, and bifunctional peptide in a buffered aqueous solution at a pH in a range of 6-9 to form a mixture. In some embodiments, the method additionally includes agitating the mixture causing the formation of dendritic gold nanoparticles having a surface with a positive charge and having the second end portion of the bifunctional peptide exposed on the surface of the dendritic gold nanoparticles.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The figures are not necessarily to scale and certain features and certain views of the figures may be shown as exaggerated in scale or in schematic in the interest of clarity and conciseness.

FIG. 1a shows a TEM image of dendritic gold nanoparticles (gold nanodendrites) at low magnification produced using the methods of the present disclosure.

FIG. 1b shows a TEM image of dendritic gold nanoparticles (gold nanodendrites) at high magnification produced using the methods of the present disclosure.

FIG. 2 shows an absorbance spectrum of the gold nanodendrites of FIG. 1.

FIG. 4a shows the effect of using twice of the regular concentration of the bifunctional peptide.

FIG. 4b shows the effect of using half of the regular concentration of the bifunctional peptide.

FIG. 4c shows the effect of using one-eighth of the regular concentration of the bifunctional peptide.

FIG. 5a shows the results of using MBP functional peptides in the formation of the gold nanodendrites.

FIG. 5b shows the results of using Ctrl functional peptides in the formation of the gold nanodendrites.

FIG. 5c shows the results of using Tau functional peptides in the formation of the gold nanodendrites.

FIG. 5d shows the results of using Gp100 functional peptides in the formation of the gold nanodendrites.

FIG. 5e shows the results of using CTIP functional peptides in the formation of the gold nanodendrites.

FIG. 5f shows the results of using Self functional peptides in the formation of the gold nanodendrites.

DETAILED DESCRIPTION

Figure 3A:
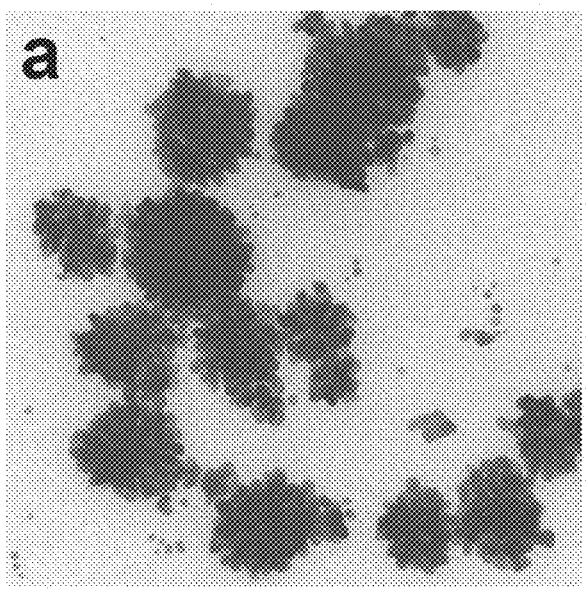
FIG. 3a shows a TEM image of gold nanoparticles illustrating dendritic structures could still be obtained when using only the structural peptide.
Figure 3B:
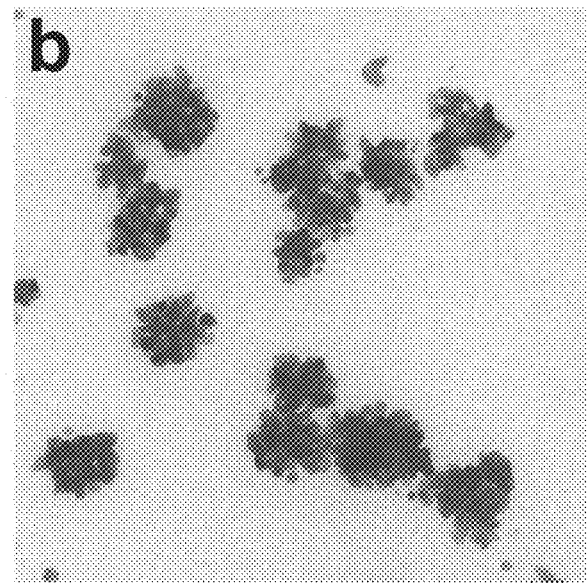
FIG. 3b shows a TEM image of gold nanoparticles illustrating dendritic structures could still be obtained when using a sham functional peptide comprising glycines.

The present disclosure is directed to novel methods of preparing dendritic gold nanoparticles, also referred to herein as gold nanoflowers or gold nanodendrites. In the novel process disclosed herein, a bifunctional peptide containing (1) an amine-rich (highly positively charged) structural amino acid sequence, and (2) a functional (e.g., therapeutic, diagnostic, targeting, immunogenic) amino acid sequence, is combined with a gold precursor composition to form functionalized dendritic gold nanoparticles having the functional peptides exposed on the surfaces thereof. The bifunctional peptide contains at least two sequences ("structural" and "functional") each having a different and special purpose. The "structural" peptide sequence serves both to induce the formation of the gold nanoparticles as nanodendrites, and to form a ligand for anchoring the "functional" peptide sequence to the exposed surfaces of the gold nanodendrites. The functional peptide comprises a variable sequence depending on the desired functionality. The functional sequence may have a therapeutic, diagnostic, targeting, and/or immunogenic purpose or any other desired function. The process thus provides for the simultaneous formation of gold nanodendrites and the functionalization of the gold nanodendrite surfaces with high density functional (e.g., therapeutic) peptides in a one-step process in aqueous solution and without reliance on the use of toxic chemicals.

The resulting functionalized gold nanodendrites can be used directly for medical applications without substantial further treatment. The gold nanodendrites disclosed herein can act as a universal platform to carry therapeutic peptides. The novel gold nanodendrites disclosed herein can also be used to deliver chemotherapeutic drugs that can be bound electrostatically to the positively-charged peptide segments without further changing the nature of the surface chemistry of the gold nanodendrites. The novel method of the present disclosure results in a lower cost method, with fewer steps and improved efficacy and stability of the product. Since no toxic chemicals are used in the disclosed method, the dendritic gold nanoparticles can be used directly for biomedical research without the need of further treatment, whereas in conventional methods, use of toxic chemicals for gold nanodendrite synthesis is almost ubiquitous, necessitating the need for additional purification treatments before use in biomedical applications. Further, the strong optical absorption of the gold nanodendrites in the near infrared region makes them ideal probes for photothermal therapy. For example, in certain embodiments, the gold nanodendrites achieve efficient photothermal cancer therapy by using a near infrared 808 or 980 nm laser. As noted, the amine-rich portion of the bifunctional peptide can be used to carry a drug component via electrostatic interaction. As such, in one embodiment, the novel gold nanodendrites can be used, for example, in a combined photothermal/chemo/immune cancer therapy.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The embodiments of the compositions, structures, and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the compositions, structures, and methods of the present disclosure have been described in terms of particular embodiments, it will be apparent to those of skill in the art that variations may be applied to the compositions, structures, and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, provisional applications, published patent applications, and non-patent publications referenced or mentioned in any portion of the present specification, including U.S. Provisional Patent Application No. 62/831,613 filed Apr. 9, 2019, are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. Any two values within the above ranges, e.g., 88 and 444 therefore can be used to set the lower and upper boundaries of a range (e.g., 88-444) in accordance with the embodiments of the present disclosure.

The term "pharmaceutically acceptable" refers to compounds, compositions, and structures which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure, "substantially pure," or "isolated" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer to a warm-blooded animal, particularly a mammal or bird. Non-limiting examples of animals within the scope and meaning of this term include dogs, cats, rats, mice, guinea pigs, horses, goats, cattle, sheep, zoo animals, Old and New World monkeys, non-human primates, and humans. The methods, compositions, kits, and systems encompassed herein may be therapeutic for the disease or condition appropriate to the composition of the functional peptide portion of the bifunctional peptide of the composition.

"Treatment" refers to therapeutic treatments. "Prevention" refers to prophylactic treatment measures to stop a condition from occurring. The term "treating" refers to administering the composition to a patient for therapeutic purposes and may result in an amelioration of the condition or disease.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent (e.g., the peptides disclosed herein) which is sufficient to exhibit a detectable chemical, biochemical and/or therapeutic effect, for example without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

The term "therapeutic" where used herein in reference to a peptide, refers to an amino acid sequence capable of bringing about a therapeutic effect when administered to a subject, for example as referred to elsewhere herein in regard to effectiveness, amelioration, or therapeutic benefits of a treatment of a diseases, condition, or disorder.

The following abbreviations may be used herein for amino acids: alanine:ala:A; arginine:arg:R; asparagine:asn:N; aspartic acid:asp:D; cysteine:cys:C; glutamic acid:glu:E; glutamine:gln:Q; glycine:gly:G; histidine:his:H; isoleucine:ile:I; leucine:leu:L; lysine:lys:K; methionine:met:M; phenylalanine:phe:F; proline:pro:P; serine:ser:S; threonine:thr:T; tryptophan:trp:W; tyrosine:tyr:Y; and valine:val:V.

The term "analog" means a chemically related form of that amino acid having a different configuration, for example, an isomer, or a D-configuration rather than an L-configuration, or an organic molecule with the approximate size and shape of the amino acid, or an amino acid with modification to the atoms that are involved in the peptide bond, to confer resistance to peptidases and proteases to a peptide. The phrases "amino acid" and "amino acid sequence" include one or more components which are amino acid derivatives and/or amino acid analogs comprising part or the entirety of the residues for any one or more of the 20 naturally-occurring amino acids indicated by that sequence. For example, in an amino acid sequence having one or more tyrosine residues, a portion of one or more of those residues can be substituted with homotyrosine.

The term "peptide" is used herein to designate a series of amino acid residues, connected one to the other typically by peptide bonds between the alpha-amino and carbonyl groups of the adjacent amino acids to form an amino acid sequence. In certain non-limiting embodiments, the peptides can range in length from 2 to 10 to 15 to 25 to 40 to 60 to 75 to 100 amino acids, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A peptide conjugate refers, in a non-limiting embodiment, to a compound comprising a peptide of the present disclosure which is conjugated (e.g., covalently linked, directly or indirectly via a linker sequence) to another atom (e.g., gold) or molecule, such as a carrier molecule such as a protein or other polymeric molecule, e.g., a polyethylene glycol (PEG) molecule, or other therapeutic compound such as a drug, or an imaging or diagnostic moiety and wherein the peptide retains its activity (e.g., binding, targeting, imaging, etc) even when conjugated to the molecule. A "fusion protein" or "fusion polypeptide" refers to proteins or polypeptides (and may be used interchangeably) which have been created by recombinant or synthetic methods to combine peptides in a serial configuration. The peptides of the present disclosure may be produced using any nucleotide sequence which encodes the desired amino acid sequence. Any of the peptides described herein or active variants thereof may be used to make the peptide-containing compositions of the present disclosure.

Peptides of the present disclosure and the nucleic acids which encode them include peptide and nucleic acid variants which comprise substitutions (conservative or non-conservative) of the native amino acids or bases. For example, the peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein.

Amino acids are classified into "groups" having chemically similar structures and chemical properties. The term "hydrophobic" amino acid means a group of aliphatic amino acids alanine (A or ala), glycine (G or gly), isoleucine (I or ile), leucine (L or leu), proline (P or pro), and valine (V or val), the terms in parentheses being the one letter and three letter standard code abbreviations for each amino acid, and a group of aromatic amino acids includes tryptophan (W or trp), phenylalanine (F or phe), and tyrosine (Y or tyr). These amino acids confer hydrophobicity as a function of the length of aliphatic and size of aromatic side chains in an amino acid sequence. The term "hydrophilic" amino acid means a group of amino acids including arginine (R or arg), asparagine (N or asn); aspartic acid (D or asp), glutamine acid (E or glu); glutamine (Q or gln), histidine (H, his), lysine (K or lys), serine (S or ser), and threonine (T or thr).

The term "neutral" amino acid means a group of amino acids including alanine (A or ala), asparagine (N or asn), cysteine (C or cys), glutamine (Q or gln), glycine (G or gly), isoleucine (I or ile), leucine (L or leu), methionine (M or met), phenylalanine (F or phe), proline (P or pro), serine (S or ser), threonine (Tor thr), tyrosine (Y or tyr), tryptophan (W or tip), and valine (V or val). The term "acidic" amino acid means a group of amino acids including aspartic acid (D or asp) and glutamic acid (E or glu). The term "basic" amino acids includes a group including arginine (R or arg), histidine (H or his), and lysine (K or lys).

The term "charged" amino acid means a group of amino acids including aspartic acid (D or asp), glutamic acid (E or glu), histidine (H or his), arginine (R or arg) and lysine (K or lys), which confer a positive (his, lys, and arg) or a negative (asp, glu) charge at physiological values of pH in aqueous solutions of peptides. The term "polar" amino acid means a group of amino acids including arginine (R or arg), lysine (K or lys), aspartic acid (D or asp), glutamine acid (E or glu), asparagine (N or asn), and glutamine (Q or gln).

One of ordinary skill in the art would readily know how to make, identify, select or test such variants for receptor targeting activity against the same receptors targeted by the native peptides. Particular examples of conservative amino acid substitutions include, but are not limited to, gly:ala substitutions; val:ile:leu substitutions; asn:glu:his substitutions; asp:glu substitutions; ser:thr:met substitutions; lys:arg:his substitutions; and phe:tyr:trp substitutions. Other types of substitutions, variations, additions, deletions and derivatives that result in functional variant peptides are also encompassed by the present disclosure, and one of skill in the art would readily know how to make, identify, or select such variants or derivatives, and how to test for receptor binding activity of those variants.

Further examples of conservative amino acid substitutions include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met. Conservative substitutions include amino acid substitution of one or more amino acid residues with another amino acid from the same group. Peptides include one or more amino acid deletions or amino acid additions of amino acids internally or to the N-terminus and C-terminus.

The term "homologous" or "% identity" as used herein means a nucleic acid (or fragment thereof) or a peptide having a degree of homology to the corresponding natural reference nucleic acid or peptide that may be in excess of 60%, or in excess of 65%, or in excess of 70%, or in excess of 75%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%, or other specific percentages described herein. For example, in regard to peptides, the percentage of homology or identity as described herein is typically calculated as the percentage of amino acid residues found in the smaller of the two sequences which align with identical amino acid residues in the sequence being compared, when four gaps per 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

In at least one embodiment "% identity" represents the number of amino acids or nucleotides which are identical at corresponding positions in two sequences of a peptide or nucleic acids encoding similar peptides. For example, two amino acid sequences each having 12 residues will have at least 75% identity when at least 9 of the amino acids at corresponding positions are the same, at least 83% identity when at least 10 of the amino acids at corresponding positions are the same, or at least 92% identity when at least 11 of the amino acids at corresponding positions are the same.

Where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

The terms "polynucleotide sequence" or "nucleic acid," as used herein, include any polynucleotide sequence which encodes a peptide product including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The peptide may be expressed using polynucleotide sequence(s) which differ in codon usage due to the degeneracies of the genetic code or allelic variations.

The terms "infection," "transduction," and "transfection" are used interchangeably herein and mean introduction of a gene, nucleic acid, or polynucleotide sequence into cells such that the encoded peptide or protein is expressed. The polynucleotides which encode peptides or proteins of the present disclosure may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more peptide molecules described herein. Expression vectors for different cell types are well known in the art and can be selected without undue experimentation. Generally, the DNA encoding the fusion polypeptide is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g., in Sambrook et al. Molecular Cloning: A Laboratory Manual, 3d ed., Cold Spring Harbor Laboratory Press, NY 2001)).

In at least certain embodiments, the peptide-containing compositions of the present disclosure, whether wholly or partially synthetically or recombinantly produced, may be used as a pharmaceutical composition when combined with a pharmaceutically acceptable carrier. Such a composition may contain, in addition to the peptide-containing composition and carrier, diluents, fillers, salts, buffers, stabilizers, solubilizers, and other materials well known in the art. Suitable carriers, vehicles and other components of the formulation are described, for example, in Remington: The Science and Practice of Pharmacy, $22^{nd}$ ed. The term "pharmaceutically acceptable" means a non-toxic material that does not interfere with the effectiveness of the biological activity of the peptide-containing composition. The characteristics of the carrier will depend on the route of administration.

Pharmaceutical compositions of the present disclosure may be in the form of liposomes in which the peptide-containing composition is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

In certain embodiments, an effective amount of the peptide-containing composition described herein may be used for treatment of a particular condition which would benefit from the biological activity of the peptide(s therein. The effective amount can be determined by the attending diagnostician, as one skilled in the art, by the use of conventional techniques and by observing results obtained under analogous circumstances. In determining the therapeutically effective dose, a number of factors may be considered by the attending diagnostician, including, but not limited to: the species of the subject; its size, age, and general health; the response of the individual subject; the mode of administration; the bioavailability characteristic of the preparation administered; the dose regimen selected; the use of concomitant medication; and other relevant circumstances. An effective amount of a peptide-containing composition of the present disclosure also refers to an amount of the peptide-containing composition which is effective in controlling or reducing the particular condition.

An effective amount of a composition of the present disclosure will generally contain sufficient active ingredient (i.e., the functional peptide) to deliver from about 0.1 µg/kg to about 100 mg/kg (weight of active ingredient/body weight of patient). Particularly, the composition will deliver at least 0.5 µg/kg to 50 mg/kg, and more particularly at least 1 µg/kg to 10 mg/kg. Without wishing to be held to a specific dosage, it is contemplated that the various pharmaceutical compositions used to practice the method of the present disclosure may contain, but are not limited to, about 0.01 mg to about 25 mg of the functional peptide per kg body weight per dose.

Practice of the method of the present disclosure may include administering to a subject an effective amount of the peptide-containing composition in any suitable systemic or local formulation, in an amount effective to deliver the dosages listed above, including but not limited to an implantable material. In one embodiment, an effective, particular therapeutic dosage of the peptide is 1 µg/kg to 10 mg/kg. The dosage can be administered on a one-time basis, or (for example) from one to five times per day or once or twice per week, or continuously via a venous drip, depending on the desired therapeutic effect. In one therapeutic method of the present disclosure, the peptide is provided in an IV infusion in the range of from 1 mg/kg-10 mg/kg of body weight once a day. The duration of an intravenous therapy using the pharmaceutical composition of the present disclosure will vary, depending on the condition being treated and the condition and potential idiosyncratic response of each individual patient. In at least one embodiment, it is contemplated that the duration of each application of the peptide may be in the range of 1 to 4 hours and given once every 12 or 24 hours by continuous intravenous administration. Other therapeutic drugs, intravenous fluids, cardiovascular and respiratory support could also be provided if requested by the attending physician in a manner known to one of ordinary skill in the art.

In practicing the method of treatment or use of the peptide-containing composition of the present disclosure, an effective amount of the peptide-containing composition is administered to a mammal having a condition to be treated. The peptide-containing composition may be administered in accordance with the method of the present disclosure either alone or in combination with other therapies.

Administration of the peptide-containing composition or practice of the method of the present disclosure can be carried out in a variety of conventional ways, such as, but not limited to, orally, by inhalation, rectally, or by cutaneous, subcutaneous, intraperitoneal, vaginal, or intravenous injection, or via implantation of a scaffold or other implantable structure.

When an effective amount of the peptide-containing composition is administered orally, the compound may be in the form of a tablet, capsule, powder, solution or elixir. The peptide-containing composition may additionally contain a solid carrier such as a gelatin or an adjuvant. The tablet, capsule, and powder particularly contains from about 0.05 to 95% of the peptide-containing composition by weight. When administered in liquid form, a liquid carrier such as water, petroleum, oils of animal or plant origin such as peanut oil, mineral oil, soybean oil, or sesame oil, or synthetic oils may be added. The liquid form of the peptide-containing composition may further contain physiological saline solution, dextrose or other saccharide solution, or glycols such as ethylene glycol, 35 propylene glycol or polyethylene glycol. When administered in liquid form, the peptide-containing composition particularly contains from about 0.005 to 95% by weight of peptide. For example, a dose of 10-1000 mg once to twice a day could be administered orally.

For oral administration, the peptide-containing composition can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the peptide-containing composition of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the peptide-containing composition in an aqueous or non-aqueous pharmaceutically acceptable solvent which may also contain suspending agents, sweetening agents, flavoring agents, and preservative agents as are known in the art.

For parenteral administration, for example, the peptide-containing composition may be suspended in a physiologically acceptable pharmaceutical carrier and administered as either a solution or a dispersion. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

When an effective amount of the peptide-containing composition is administered by intravenous, cutaneous or subcutaneous injection, the peptide-containing composition may be in the form of a pyrogen-free, parenterally acceptable aqueous solution or suspension. The preparation of such parenterally-acceptable solutions, having due regard to pH, isotonicity, stability, and the like, is within the skill in the art. A particular pharmaceutical composition for intravenous, cutaneous, or subcutaneous injection may contain, in addition to the peptide-containing composition, an isotonic vehicle such as Sodium Chloride Injection, Ringer's Injection, Dextrose Injection, Dextrose and Sodium Chloride Injection, Lactated Ringer's Injection, or other vehicle as known in the art. The peptide-containing composition of the present disclosure may also contain stabilizers, preservatives, buffers, antioxidants, or other additive known to those of skill in the art.

As noted above, the peptide-containing composition can also include an appropriate carrier. For surgical implantation, the peptide-containing composition may be combined with any of the well-known biodegradable and bioerodible carriers, such as polylactic acid and collagen formulations. Such materials may be in the form of solid implants, sutures, sponges, wound dressings, and the like. In any event, for local use of the materials, the peptide-containing composition is usually present in the carrier or excipient in a weight ratio of from about 1:1000 to 1:20,000, but is not limited to ratios within this range. Preparation of compositions for local use is detailed in Remington: The Science and Practice of Pharmacy, $22^{nd}$ ed.

As noted, particular amounts and modes of administration are able to be determined by one skilled in the art. One skilled in the art of preparing formulations can readily select the proper form and mode of administration depending upon the particular characteristics of the peptide-containing composition selected, the condition to be treated, and other relevant circumstances using formulation technology known in the art, described, for example, in Remington: The Science and Practice of Pharmacy, $22^{nd}$ ed. The pharmaceutical compositions of the present disclosure can be manufactured utilizing techniques known in the art. As noted above, typically the effective amount of the peptide-containing composition will be admixed with a pharmaceutically acceptable carrier.

Additional pharmaceutical methods may be employed to control the duration of action of the peptide-containing composition. Increased half-life and controlled release preparations may be achieved through the use of polymers to conjugate, complex with, or absorb the peptide-containing composition described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, proteins (e.g., bovine serum albumin or human serum albumin) and the appropriate concentration of macromolecules as well as the methods of incorporation, in order to control release.

Another possible method useful in controlling the duration of action by controlled release preparations and half-life is incorporation of the peptide-containing composition into particles of a polymeric material such as polyesters, polyamides, polyamino acids, hydrogels, poly(lactic acid), ethylene vinylacetate copolymers, copolymer micelles of, for example, PEG and poly(l-aspartamide).

It is also possible to entrap the peptide-containing composition in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the peptide-containing composition is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The peptide-containing composition may also be in the form of an aqueous solution containing many of the same substances as described above for the reconstitution of a lyophilized product.

In certain embodiments the peptide-containing composition of the present disclosure can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the peptide-containing composition of the present disclosure may be incorporated into pharmaceutical preparations which may be used for therapeutic purposes, including vaccines. However, the term "pharmaceutical preparation" is intended in a broader sense herein to include preparations containing a peptide-containing composition in accordance with present disclosure, used not only for therapeutic purposes but also for reagent, imaging, or diagnostic purposes as known in the art. The pharmaceutical preparation intended for therapeutic use should contain a "pharmaceutically acceptable" or "effective amount" of the peptide-containing composition, i.e., that amount necessary for a therapeutic response in a patient or subject in need of such treatment. If the peptide-containing composition is to be employed as a reagent, imaging, or diagnostic, then it should contain reagent, imaging, or diagnostic amounts of the peptide.

Synthesis of gold nanoflowers (gold nanodendrites) used herein may be carried out in a single step ("one pot") by combining and mixing a gold precursor (e.g., $HAuCl_4$ and/or salts thereof such as $NaAuCl_4$ and $KAuCl_4$), a bifunctional peptide (e.g., as shown in Table 2), and a reducing agent (e.g., ascorbic acid, sodium ascorbate, hydrazine, hydroxylamine, and/or any other suitable mild reducing agent) in an aqueous buffer solution at a suitable pH (e.g., in a range of 6-9), followed by gentle agitation (e.g., on a rocker shaker, by vortex, hand shaking, or magnetic stirring, or in some cases without agitation)) for at least about 5 minutes to 60 min, or longer. Buffers that may be used include, but are not limited to, HEPES, MES, Bis-Tris, ADA, ACES, PIPES, MOPSO, BES, MOPS, TES, MOBS, TAPSO, EPPS, Tricine buffer, Gly-Gly buffer, Bicine buffer, TAPS, AMPD, TABS, AMPSO, CHES, and CAPSO.

Structural peptides used herein to form the bifunctional peptides of the disclosure may comprise from 2 to 16 or more positively-charged amino acids. For example, the structural peptide may have the sequence $X_1$-$X_2$-$X_3$-$X_4$-$X_5$-$X_6$-$X_7$-$X_8$ (SEQ ID NO:53), wherein each of $X_1$-$X_8$ is independently selected from Arg (R), Lys (K), and His (H), wherein each 8-mer peptide contains from 0 to 8 R, 0 to 8 K, and 0 to 8 H, in any arrangement. For example, 8-mer amine-rich structural peptides of the present disclosure include, but are not limited to, amino acid sequences shown in Table 1.

TABLE 1

Examples of 8-mer Structural (amine-rich) Peptides

| SEQ ID No. | Sequence |
| --- | --- |
| 1 | R-R-R-R-R-R-R-R |
| 2 | R-R-R-R-R-R-R-K |
| 3 | K-R-R-R-R-R-R-R |
| 4 | K-R-R-R-R-R-R-K |
| 5 | R-K-R-R-R-R-K-R |
| 6 | R-R-K-R-R-R-K-R |
| 7 | R-R-R-K-K-R-R-R |
| 8 | R-K-K-R-R-K-K-R |
| 9 | K-R-K-R-K-R-K-R |
| 10 | R-K-R-K-R-K-R |
| 11 | R-R-R-K-K-R-R-K |
| 12 | K-R-R-K-K-R-R-R |
| 13 | R-R-R-K-K-R-R-K |
| 14 | K-R-R-K-K-R-R-R |
| 15 | R-R-R-R-K-K-K-K |

TABLE 1-continued

Examples of 8-mer Structural (amine-rich) Peptides

| SEQ ID No. | Sequence |
| --- | --- |
| 16 | R-K-K-K-K-K-K-R |
| 17 | R-R-R-R-R-R-R-H |
| 18 | H-R-R-R-R-R-R-R |
| 19 | H-R-R-R-R-R-R-H |
| 20 | R-H-R-R-R-R-H-R |
| 21 | R-R-H-R-R-H-R-R |
| 22 | R-R-R-H-H-R-R-R |
| 23 | R-H-H-R-R-H-H-R |
| 24 | H-R-H-R-H-R-H-R |
| 25 | R-H-R-H-R-H-R-H |
| 26 | R-R-R-H-H-R-R-H |
| 27 | H-R-R-H-H-R-R-R |
| 28 | R-R-R-H-H-R-R-H |
| 29 | H-R-R-H-H-R-R-R |
| 30 | R-R-R-R-H-H-H-H |
| 31 | R-H-H-H-H-H-H-R |
| 32 | H-H-H-H-H-H-H-H |
| 33 | K-K-K-K-K-K-K-K |
| 34 | K-K-K-K-K-K-K-H |
| 35 | H-K-K-K-K-K-K-K |
| 36 | H-K-K-K-K-K-K-H |
| 37 | K-H-K-K-K-K-H-K |
| 38 | K-K-H-K-K-H-K-K |
| 39 | K-K-K-H-H-K-K-K |
| 40 | K-H-H-K-K-H-H-K |
| 41 | H-K-H-K-H-K-H-K |
| 42 | K-H-K-H-K-H-K-H |
| 43 | K-K-K-H-H-K-K-H |
| 44 | H-K-K-H-H-K-K-K |
| 45 | K-K-K-H-H-K-K-H |
| 46 | H-K-K-H-H-K-K-K |
| 47 | K-K-K-K-H-H-H-H |
| 48 | K-H-H-H-H-H-H-K |

In alternate embodiments, the structural peptide may have the sequence $X_1$-$X_2$, wherein each of $X_1$-$X_2$ is independently selected from Arg (R), Lys (K), and His (H), wherein each 2-mer peptide contains from 0 to 2 R, 0 to 2 K, and 0 to 2 H, in any arrangement.

In alternate embodiments, the structural peptide may have the sequence $X_1$-$X_2$-$X_3$, wherein each of $X_1$-$X_3$ is independently selected from Arg (R), Lys (K), and His (H), wherein each 3-mer peptide contains from 0 to 3 R, 0 to 3 K, and 0 to 3 H, in any arrangement.

In alternate embodiments, the structural peptide may have the sequence $X_1$-$X_2$-$X_3$-$X_4$ (SEQ ID NO:49), wherein each of $X_1$-$X_4$ is independently selected from Arg (R), Lys (K), and His (H), wherein each 4-mer peptide contains from 0 to 4 R, 0 to 4 K, and 0 to 4 H, in any arrangement.

In alternate embodiments, the structural peptide may have the sequence $X_1$-$X_2$-$X_3$-$X_4$-$X_5$ (SEQ ID NO:50), wherein each of $X_1$-$X_5$ is independently selected from Arg (R), Lys (K), and His (H), wherein each 5-mer peptide contains from 0 to 5 R, 0 to 5 K, and 0 to 5 H, in any arrangement.

In alternate embodiments, the structural peptide may have the sequence $X_1$-$X_2$-$X_3$-$X_4$-$X_5$-$X_6$ (SEQ ID NO:51), wherein each of $X_1$-$X_6$ is independently selected from Arg (R), Lys (K), and His (H), wherein each 6-mer peptide contains from 0 to 6 R, 0 to 6 K, and 0 to 6 H, in any arrangement.

In alternate embodiments, the structural peptide may have the sequence $X_1$-$X_2$-$X_3$-$X_4$-$X_5$-$X_6$-$X_7$ (SEQ ID NO:52), wherein each of $X_1$-$X_7$ is independently selected from Arg (R), Lys (K), and His (H), wherein each 7-mer peptide contains from 0 to 7 R, 0 to 7 K, and 0 to 7 H, in any arrangement.

In alternate embodiments, the structural peptide may have the sequence $X_1$-$X_2$-$X_3$-$X_4$-$X_5$-$X_6$-$X_7$-$X_8$-$X_9$ (SEQ ID NO:54), wherein each of $X_1$-$X_9$ is independently selected from Arg (R), Lys (K), and His (H), wherein each 9-mer peptide contains from 0 to 9 R, 0 to 9 K, and 0 to 9 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$ (SEQ ID NO:55), wherein each of $X_1$-$X_{10}$ is independently selected from Arg (R), Lys (K), and His (H), wherein each 10-mer peptide contains from 0 to 10 R, 0 to 10 K, and 0 to 10 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$-$X_{11}$ (SEQ ID NO:56), wherein each of $X_1$-$X_{11}$ is independently selected from Arg (R), Lys (K), and His (H), wherein each 11-mer peptide contains from 0 to 11 R, 0 to 11 K, and 0 to 11 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$-$X_{11}$-$X_{12}$ (SEQ ID NO:57), wherein each of $X_1$-$X_{12}$ is independently selected from Arg (R), Lys (K), and His (H), wherein each 12-mer peptide contains from 0 to 12 R, 0 to 12 K, and 0 to 12 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$-$X_{11}$-$X_{12}$-$X_{13}$ (SEQ ID NO: 58), wherein each of $X_1$-$X_{13}$ is independently selected from Arg (R), Lys (K), and His (H), wherein each 13-mer peptide contains from 0 to 13 R, 0 to 13 K, and 0 to 13 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$ (SEQ ID NO:59), wherein each of $X_1$-$X_{14}$ is independently selected from Arg (R), Lys (K), and His (H), wherein each 14-mer peptide contains from 0 to 14 R, 0 to 14 K, and 0 to 14 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ (SEQ ID NO:60), wherein each of $X_1$-$X_{16}$ is independently selected from Arg (R), Lys (K), and His (H), wherein each 15-mer peptide contains from 0 to 15 R, 0 to 15 K, and 0 to 15 H, in any arrangement.

In alternate embodiments, the structural peptide may have the sequence $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$ (SEQ ID NO:61), wherein each of $X_1$-$X_{16}$ is independently selected from Arg (R), Lys (K), and His (H), wherein each 16-mer peptide contains from 0 to 16 R, 0 to 16 K, and 0-16 H, in any arrangement.

In certain embodiments, the amine-rich structural peptide may optionally be linked to the therapeutic peptide via an intermediate amino acid linker sequence of, for example, 1 to 100 additional amino acids, (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids). The linker sequence may extend from the N-terminal or C-terminal end of the structural peptide or the therapeutic peptide The amino acids of the linker sequence may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, and other natural or non-natural amino acids.

Various embodiments of the present disclosure will be more readily understood by reference to the following examples and description, which as noted above are included merely for purposes of illustration of certain aspects and embodiments of the present disclosure, and are not intended to be limiting. The following detailed examples and methods describe how to make and use various peptides and nanodendritic particles of the present disclosure and are to be construed, as noted above, only as illustrative, and not limitations of the disclosure in any way whatsoever. Those skilled in the art will promptly recognize appropriate variations from the materials and procedures described herein.

EXAMPLES

Example 1

Gold nanodendrites were produced using a bifunctional peptide comprising an 8-mer arginine sequence ($R_8$) as the structural peptide, and various other sequences as the functional peptide. Non-limiting examples of the functional peptides that can be used are shown in Table 2. Any functional peptide sequence known in the art which functions in accordance with the present disclosure can be used in place of the peptides shown in Table 2.

TABLE 2

List of the tested functional peptides

| Name (SEQ ID NO:) | Sequence | Function |
|---|---|---|
| NFL (SEQ ID NO: 62) | YSSSAPVSSSVRRSYSSSGS | Tubulin binding |
| G23 (SEQ ID NO: 63) | GGGGGGGGGGGGGGGGGGGG | Control |
| MBP (SEQ ID NO: 64) | AREYGTRFSLIGGYR | MCF7 targeting |
| Ctrl (SEQ ID NO: 65) | RGIEFYGRSTLAAGR | MBP scrambled |
| Gp100 (SEQ ID NO: 66) | IMDQVPFSV | Melanomaantigen peptide vaccine |
| Tau (SEQ ID NO: 67) | VQIINKKLDLSNVQS | Tubulin binding |
| CTIP (SEQ ID NO: 68) | DGSIPWST | SKBR-3 binding and internalizing |
| Self (SEQ ID NO: 69) | NYTCEVTELTREGETIIELK | Inhibitor of phagocyte clearance |
| Dermicidin (SEQ ID NO: 70) | SSLLEKGLDGAKKAVGGLGKLGKDA | Antibacterial |
| OVA (SEQ ID NO: 71) | ISQAVHAAHAEINEAGR | Antigen epitope of ovalbumin protein |

The functional peptides of Table 2 were linked via a GGG or GGGG (SEQ ID NO:72) linker (except CTIP) to a structural peptide comprising 8 consecutive arginine residues, RRRRRRRR ($R_8$), as shown in Table 3.

TABLE 3

Examples of Bifunctional peptides

| Name (SEQ ID NO:) | Amino acid Sequence* | Function of Functional peptide |
|---|---|---|
| $R_8$+NFL (SEQ ID NO: 73) | RRRRRRRRGGGYSSSAPVSSSVRRSYSSSGS | Tubulin binding |

TABLE 3-continued

Examples of Bifunctional peptides

| Name (SEQ ID NO:) | Amino acid Sequence* | Function of Functional peptide |
|---|---|---|
| MBP+$R_8$ (SEQ ID NO: 74) | AREYGTRFSLIGGYRGGGRR RRRRRR | MCF7 cell targeting |
| Ctrl+$R_8$ (SEQ ID NO: 75) | RGIEFYGRSTLAAGRGGGRR RRRRRR | Scrambled control version of MBP |
| $R_8$+Gp100 (SEQ ID NO: 76) | RRRRRRRRGGGIMDQVPFSV | Melanoma antigen for peptide vaccine |
| $R_8$+Tau (SEQ ID NO: 77) | RRRRRRRRGGGVQIINKKLD LSNVQS | Tubulin binding |
| $R_8$+Self (SEQ ID NO: 78) | RRRRRRRRGGGGNYTCEVT ELTREGETIIELK | Inhibit phagocytic clearance |
| $R_8$+ Derm (SEQ ID NO: 79) | RRRRRRRRGGGSSLLEKGLD GAKKAVGGLGKLGKDA | Antibacterial |
| $R_8$+OVA (SEQ ID NO: 80) | RRRRRRRRGGGISQAVHAAH AEINEAGR | Antigen epitope of ovalbumin protein |
| CTIPs+$R_8$ (SEQ ID NO: 81) | DGSIPWSTRRRRRRRR | SKBR-3 cell binding and internalizing peptide |
| G23 (SEQ ID NO: 82) | RRRRRRRRGGGGGGGGGGG GGGGGGGGGG | Control |

*The structural peptide component of each bifunctional is represented as a sequence of 8 arginine residues. Functional peptides were linked, in most cases, to the structural peptide via a GGG or GGGG linker sequence.

Methods: Gold chloride ($HAuCl_4$, 99.9%) was purchased from Strem Chemicals. Ascorbic acid (98%) and HEPES (99.5%) were purchased from Sigma-Aldrich. Peptides were synthesized at United Peptide with the purity >90%. All chemicals were used as received.

Synthesis of gold nanoflowers (gold nanodendrites) was carried out simply by combining and mixing $HAuCl_4$, a bifunctional peptide (e.g., as shown in Table 2), and a reducing agent in an aqueous buffer solution, followed by gentle shaking for about 20 min. More specifically, 500 μl of 50 mM pH 7.4 Hepes buffer, 10 μl of 5 mM bifunctional peptide, 2.5 μl of 60 mM $HAuCl_4$ and 20 μl of 88 mM ascorbic acid were added in succession into a reaction vial. The solutions were then mixed vigorously by hand for a few seconds, and then left on a rocker shaker for about 20 min, during which gold nanoflowers are formed. A deep blue or black colored solution indicates the formation of the gold nanoflowers. The nanoparticles were then centrifuged and redispersed into 500 μl of DI $H_2O$. The structural peptide comprised the sequence $R_8$. Several different functional peptides (Table 1) were used to form the bifunctional peptides (Table 2) used in the example. Following above synthesis procedure, gold nanoflower structures were obtained when using all the listed peptides, demonstrating the generality and customizability of the presently disclosed synthetic approach.

Figure 3C:
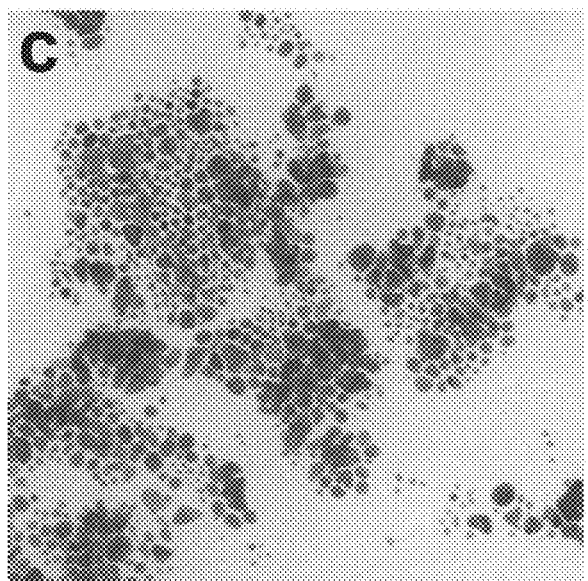
FIG. 3c shows a TEM image illustrating the sham peptide alone could not produce the dendritic nanoparticles.
Figure 3D:
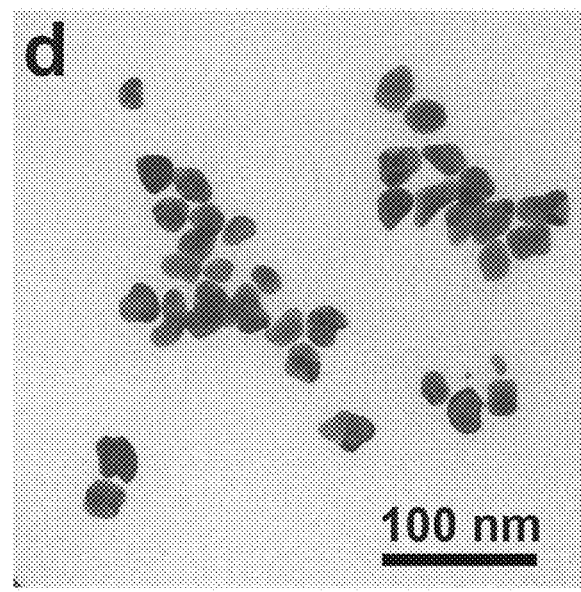
FIG. 3d shows a TEM image illustrating when no peptide was used only solid gold nanoparticles could be synthesized.

Results: Regarding the structure and spectrum of the gold nanoparticles produced using the present methods, FIG. 1 shows TEM images of gold dendritic nanoparticles at low magnification (A) and higher magnification (B). The gold nanodendrites were manufactured using a bifunctional peptide comprising an eight-arginine functional peptide linked to an NFL functional peptide (Table 2). FIG. 2 shows an absorbance spectrum of the gold nanodendrites of FIG. 1 demonstrating a broadband absorption. The roles of the structural vs. functional peptide in synthesis of gold nanoparticles were investigated. When only an $R_8$ peptide was used in place of a bifunctional peptide, or when a bifunctional peptide with a sham functional peptide ($Gly_{20}$) plus $R_8$ was used, dendritic gold nanoparticles were produced (FIG. 3 A-B, respectively). When only the sham functional peptide was used ($Gly_{20}$), gold nanodendrites were not produced (FIG. 3C). When no peptides were used, only solid gold nanoparticles were synthesized (FIG. 3D). The effects of peptide concentration were then examined. Using peptide concentrations of 2× and 0.5× uniform gold nanodendrites were still produced (FIG. A, B, respectively), but with a slightly different morphology than those produced at the normal 1× concentration (5 mM). A peptide concentration of 0.125× was insufficient to induce well-dispersed and uniform gold nanodendrites (FIG. 4C). Only irregularly branched and aggregated nanoparticles could be formed. The effect of differences in the functional peptide component of the bifunctional peptide was then investigated. Typical gold nanodendrite structures formed using various biofunctional peptides of Table 2 are shown FIG. 5. All bifunctional peptides, containing the amine-rich peptide $R_8$, resulted in the production of dendritic gold nanoparticles, confirming that it is the amine-rich peptide portion of the bifunctional peptide that is necessary for the production of the gold nanodendrites (gold nanoflowers).

In summary, using a simple one-step reaction, multifunctional dendritic gold nanoparticles can be synthesized using bifunctional peptides comprising an amine-rich portion. Through tuning the peptides in the functional segment, the biofunctionality of the gold nanodendrites can be customized. Together with the large surface area, efficient drug loading capability and strong photothermal effect, these gold nanodendrites can be used as a powerful and broadly-applicable therapeutic delivery mechanism.

Example 2

Figure 6A:
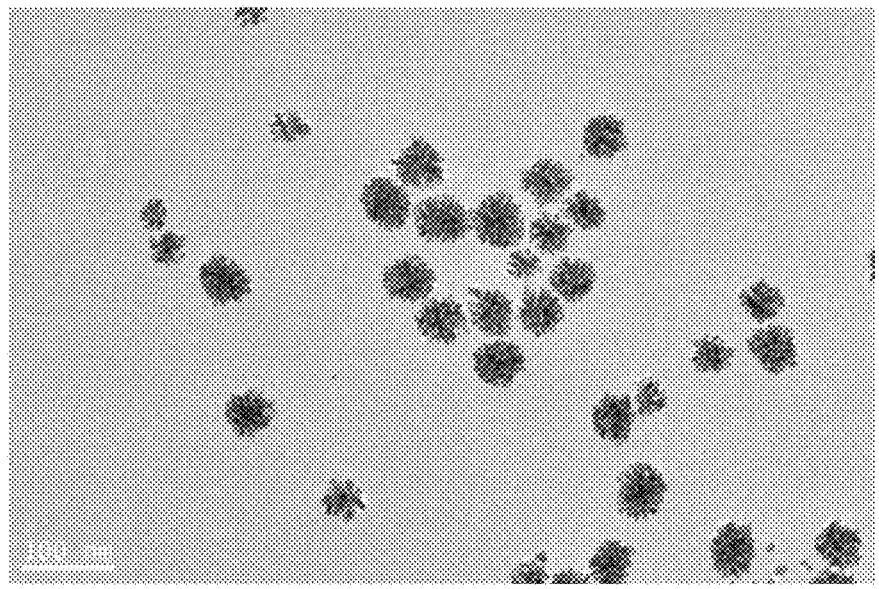
FIG. 6a shows a TEM image of gold nanodendrites fabricated with R8+Trp2 peptide at low magnification. Diameters are about 50 nm and are full of branches.
Figure 6B:
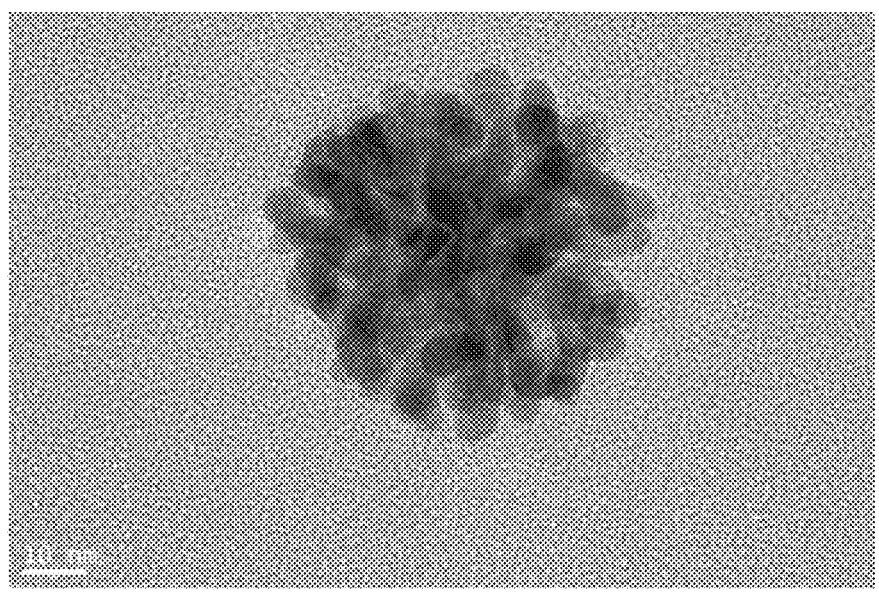
FIG. 6b shows a TEM image of gold nanodendrites fabricated with R8+Trp2 peptide at high magnification. Diameters are about 50 nm and are full of branches.

Gold Nanodendrites as a Vaccine Formulation. In this example, the gold nanodendrites (a.k.a., gold nanoflowers, or AuNFs) were used to manufacture a nanovaccine for melanoma cancer immunotherapy. For this application, the gold nanodendrites were made using a bifunctional peptide comprising $R_8$ as the structural peptide (as above) and Trp2 peptide (SYYDFFVWL—SEQ ID NO:83)) as the functional peptide. Trp2 is a reported melanoma antigen peptide. Examples of the produced $R_8$-Trp2 gold nanodendrites are shown in FIG. 6.

The $R_8$-Trp2 gold nanodendrites were then coated with a CpG oligodeoxynucleotide ("CpG"), a strong adjuvant which can stimulate dendritic cell maturation and drive efficient immune responses, through electrostatic interaction. CpG is a synthetic DNA containing a cytosine triphosphate deoxynucleotide, "C", followed by a guanine triphosphate deoxynucleotide, "G". In one version, used herein, the oligodeoxynucleotide has the sequence 5'-tc-catgacgttcctgacgtt-3'. It possesses a negative charge, thus the molecule can be loaded on the positive AuNFs through electrostatic interactions.

Figure 7:
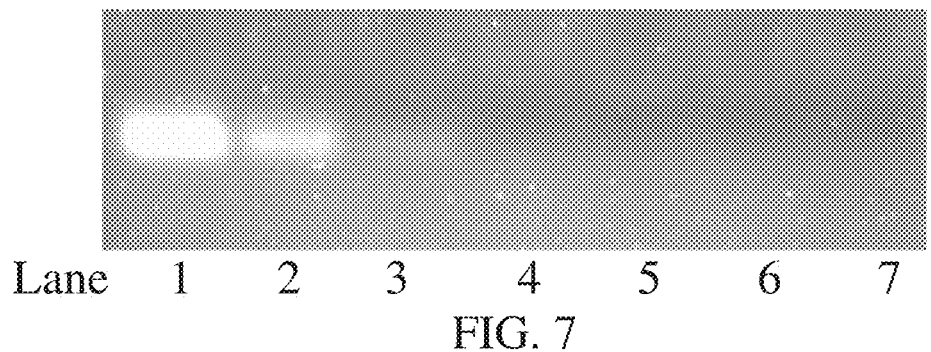
FIG. 7 is a photograph of an agarose electrophoresis gel which confirms the loading of CpG oligodeoxynucleotide on the gold nanodendrites.

CpG loading on AuNFs was confirmed through agarose gel electrophoresis (FIG. 7). In a series of AuNF and CpG mixtures, shown in lanes 1 to 7 in FIG. 7, the amount of CpG was fixed at 0.5 μg and the amount of AuNFs was changed in increasing amounts from 0 to 12 μg. After a 5-hour incubation, the AuNFs with the loaded CpG were removed through centrifugation and the CpG left in the supernatant was analyzed using electrophoresis. FIG. 7, from lane 1 to 7, shows supernatants of the mixtures with the amount of Au increasing from 0, 1.5, 3, 4.5, 6, 9 and 12 µg, respectively. With the increasing of AuNFs in the mixture, the amount of unloaded CpG in the supernatant decreased dramatically, which indicates the high loading efficiency of CpG on AuNFs. The resultant gold dendritic nanoparticle functionalized with Trp2 peptide and loaded with CpG oligonucleotide was termed AuNF-Trp2-CpG. The AuNF-Trp2-CpG nanovaccine possesses multiple functions: it is an highly efficient nanocarrier of surface antigen peptides and CpG adjuvant to stimulate the immune response, and it also has a photothermal property that can be used to destroy tumors by irradiation with a laser beam. The hydrodynamic diameter of the as-prepared $R_8$+Trp2 AuNFs was about 94 nm based on the dynamic light scattering result. The zeta potential of the $R_8$+Trp2 AuNFs was about 17.1 mV, meaning the surface of nanoparticles was positively charged, indicating the presence of the coating of $R_8$ peptides on the nanoparticle surface.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the components, formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in this or subsequent patent applications.

What is claimed is:

1. A method of producing dendritic gold nanoparticles, comprising:
   providing a gold precursor solution, a reducing agent, and a bifunctional peptide, wherein the bifunctional peptide comprises a first end portion comprising an amine-rich amino acid sequence, and a second end portion;
   combining, in a single container, the gold precursor solution, reducing agent, and bifunctional peptide in a buffered aqueous solution at a pH in a range of 6-9 to form a mixture; and
   agitating the mixture causing the formation of dendritic gold nanoparticles having a surface with a positive charge and having the second end portion of the bifunctional peptide exposed on the surface of the dendritic gold nanoparticles.

2. The method of claim 1, wherein the first end portion of the bifunctional peptide comprises 2 to 16 positively-charged amino acids.

3. The method of claim 2, wherein the 2 to 16 positively-charged amino acids are selected from the group consisting of arginine (R), lysine (K), and histidine (H).

4. The method of claim 1, wherein the first end portion of the bifunctional peptide comprises the amino acid sequence $X_1$-$X_2$-$X_3$-$X_4$-$X_5$-$X_6$-$X_7$-$X_8$ (SEQ ID NO:53), wherein each of $X_1$-$X_8$ is independently selected from R, K, and H in any arrangement.

5. The method of claim 1, wherein the first end portion and the second end portion of the bifunctional peptide are directly linked via a peptide bond.

6. The method of claim 1, wherein the first end portion and the second end portion of the bifunctional peptide are linked together via an intervening linker sequence.

7. The method of claim 1, comprising coating the dendritic gold nanoparticles with a negatively-charged oligodeoxynucleotide, wherein the oligodeoxynucleotide is bound electrostatically to the dendritic gold nanoparticles.

* * * * *